United States Patent [19]

Charlton et al.

[11] Patent Number: 4,774,054

[45] Date of Patent: Sep. 27, 1988

[54] AXIALLY PROTECTED TEST STRIPS

[75] Inventors: Steven Charlton, Elkhart, Ind.; Helmut Engelmann, Leverkusen, Fed. Rep. of Germany

[73] Assignee: Miles Inc., Elkhart, Ind.

[21] Appl. No.: 68,148

[22] Filed: Jun. 29, 1987

Related U.S. Application Data

[63] Continuation-in-part of Ser. No. 869,217, Jun. 2, 1986, abandoned.

[30] Foreign Application Priority Data

Jun. 11, 1985 [DE] Fed. Rep. of Germany ....... 3520847

[51] Int. Cl.$^4$ ............................................. G01N 31/22
[52] U.S. Cl. ........................................ 422/56; 422/57; 422/58
[58] Field of Search ................................... 422/56–58, 422/55; 436/169, 170; 435/805

[56] References Cited

U.S. PATENT DOCUMENTS

| | | | |
|---|---|---|---|
| 3,443,903 | 5/1969 | Haack et al. | 422/56 |
| 3,509,872 | 5/1970 | Truhan | 422/58 |
| 3,809,617 | 5/1974 | Schmitt | 422/56 |
| 4,230,757 | 10/1980 | Toner | 422/56 |
| 4,260,392 | 4/1981 | Lee | 422/56 |
| 4,420,353 | 12/1983 | Levine | 422/56 |

FOREIGN PATENT DOCUMENTS 2655977 6/1978 Fed. Rep. of Germany ........ 422/56

*Primary Examiner*—Benoit Castel
*Attorney, Agent, or Firm*—Roger N. Coe

[57] ABSTRACT

Test devices are disclosed in which the reagent matrix area(s) attached to a substrate are protected axially in the direction of the elongated substrate by a sloping surface(s) adjacent to each matrix area extending to the identical height of the matrix material. The resulting surface(s) protects said matrices from damage, particularly during wiping operations during which excess liquid and/or material is removed from the matrices.

3 Claims, 1 Drawing Sheet

FIG. 1
FIG. 2
FIG. 3
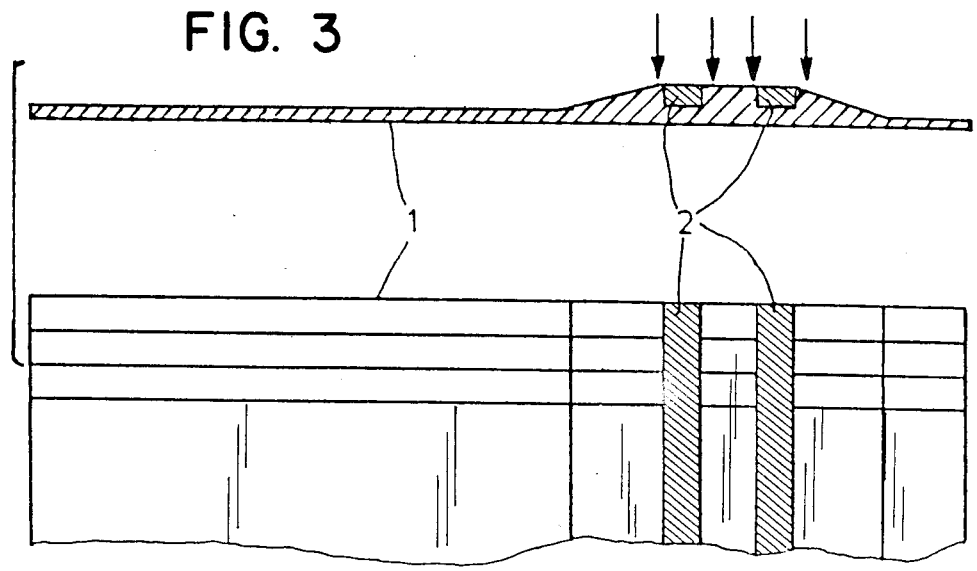

AXIALLY PROTECTED TEST STRIPS

This application is a continuation-in-part application of U.S. Ser. No. 869,217, filed June 2, 1986, now abandoned.

BACKGROUND OF THE INVENTION

The use of test devices or strips in analysis and, in particular, in clinical chemistry belongs to the established processes. In comparison with conventional methods of wet chemistry, such analyses are faster and easier to carry out.

However, when test strips are used in analysis, especially in whole blood, it is frequently necessary to wipe the strip. This wiping operation can lead to damage to the edges and surfaces of the reagent pad projecting out from the plane of the substrate. Subsequent evaluation, for example with a reflectance photometer, is thereby influenced and can lead to results which cannot be reproduced.

Typically reagent test devices contain one or more reagent matrix areas or pads attached to a substrate. The matrix areas or pads extend above the surface of the substrate and accordingly these areas or pads are exposed and tend to be damaged during (a) transport, (b) removal of the test devices from their container, and/or (c) in use, e.g., when wiping a test device to remove red blood cells, contaminants, etc. Not only are the edges of the test devices damaged, but frequently the surface of a pad is damaged. Not uncommonly, the entire pad or reagent matrix area is "knocked off" of the substrate during the wiping operation, particularly if the wiping tends to be vigorous. This has been a problem of longstanding which has required the attention of all manufacturers of diagnostic test devices.

Exact positioning of the reagent pad or matrix on the substrate carrier is also important for evaluation of the test strips with a reflectance photometer. If a planar surface is present for the substrate, there is the risk that the reagent pad will be brought out of the exact position as a result of inadequate adhesion of the adhesive which binds the pad to the substrate.

Inadequate adhesion of the adhesive can exist, for example, if the adhesive used has not yet hardened completely during production and packaging, or the adhesive ages as a result of storage.

Different adhesives can be required in reagent strips containing multiple reagent pads attached to a common substrate in order to ensure compatibility of the reagents in each pad with the particular adhesive employed. Exact metering of the amount of adhesive presents difficulties and leads to indeterminate hardening of reagent strips.

The influence of the residual solvent in the adhesive on the storage life of and change in the reagents introduced into a reagent strip can also be a disadvantage.

Another disadvantage is that adhesives can migrate into the reagent pad or matrix in an uncontrolled manner. Absorption of a defined volume of sample by the reagent strip is thus no longer guaranteed, which can lead to erroneous analytical results.

SUMMARY OF THE INVENTION

An object of the invention is to develop reagent strips in which the strips are largely protected from damage, particularly by wiping.

Another object of the invention is to secure a reagent pad or matrix to a substrate using a minimum amount of adhesive to retain the pad or matrix in a desired position.

In accordance with the present invention test devices are disclosed having a raised portion which extends to the same exact height (i.e., is coextensive with) as the reagent matrix area. Accordingly, test devices of the present invention can be wiped to remove red blood cells, etc. since the raised portion of the substrate protects the reagent pad axially in the direction of the elongated substrate. Specifically, the claimed invention is directed to a test device comprising an elongated substrate having a horizontal portion and a raised portion, wherein said raised portion slopes upwardly from said horizontal portion to a termination point and then perpendicularly downward at right angles toward a horizontal portion of the substrate to form a right angle shoulder between said horizontal portion and said raised portion such that a reagent matrix material can be precisely positioned on said horizontal portion abutting said raised portion at said right angle shoulder and wherein the height of the reagent matrix is coextensive with the raised portion at said termination point whereby the upper edge of the reagent matrix adjacent the raised portion is protected axially by the raised portion of the substrate.

Test devices or reagent strips in accordance with the present invention can consist of substrate carrier having one or more reagent pads and matrix areas, each of which is protected from damage when excess sample or material must be removed from the top of the matrix areas using a paper towel, cloth or the like to wipe across the matrix areas prior to determining visually the reaction which has occurred in the matrix area or inserting the test device into a instrument such as a reflectance photometer for such determination. As indicated above the substrate forms a ramp like structure which facilitates moving a paper towel, cloth or the like axially along a test device in the direction of the elongated substrate from the handle end to the matrix end of the test device.

In addition to protecting the surface of the matrix area or areas from wiping operations, the invention permits the precise positioning of a reagent pad or matrix onto the substrate of the reagent strip or test device. The invention further facilitates the use of a minimum amount of adhesive in order to securely mount the reagent pad or matrix onto the substrate of a test device or reagent strip.

BRIEF DESCRIPTION OF THE DRAWINGS

FIG. 1 shows an embodiment of the present invention in which the reagent pad is attached to a substrate with hot-melt adhesive;

FIG. 2 is another embodiment of the invention in which the reagent pad is attached to a substrate with double-sided adhesive tape; and FIG. 3 is a side view in cross section and partial top view of substrate material containing two reagent strips adhered to the substrate by friction prior to the subsequent separation of individual reagent strips.

DESCRIPTION OF THE PREFERRED EMBODIMENTS

Reagent substrates can be formed from any material which can be shaped, such as, hard papers, plastics, and the like. Particularly suitable are thermoplastic material such as polyethylene, polypropylene, polyamides or polyesters. An especially preferred material is Trycite ™ polystyrene film.

Generally, the reagent matrix or pad consists of filter paper, cloth, felt, porous ceramic, woven or matted glass fibers, and the like as well as other materials known in the art for use with reagent in the manufacture of reagent matrix areas for diagnostic test devices. Whatman filter paper W54, W3mm and W31et are especially preferred materials.

Indicators are incorporated into the reagent matrix in accordance with known procedures, i.e., impregnation, spraying, etc., to produce reagent test devices for determining the presence of test sample constituent such as glucose, pH, nitrite, blood, bilirubin, protein, ketone and the like. Thus, if a reagent matrix area is to be responsive to glucose it is normally incorporated with reagents such as glucose oxidase enzyme, a peroxidase enzyme and an indicator such as orthotoluidine. Such a reagent system turns blue when contacted with a liquid sample containing glucose.

The procedure normally used to attach reagent matrix area to a substrate is to use double-backed adhesive material. Alternatively, glue, cement and other adhesives have been used and covering meshes of thermoplastic material have been employed.

As illustrated in FIG. 1, reagent pad or matrix area 2 is inserted into raised portion 3 of an elongated substrate 1 and is mounted in the raised portion of the substrate using hot-melt adhesive (not shown). The raised portion 3 slopes upwardly from the horizontal handle portion of substrate 1 to a termination point and then perpendicularly downward to a depth sufficient to permit the reagent pad or matrix area 2 to be inserted to the same height as the highest portion of the raised surface 3 which slopes upwardly from substrate 1. Accordingly, the reagent matrix is positioned on a horizontal portion of the raised portion 3 abutting said raised portion at a right angle shoulder and the height of the reagent matrix 2 is coextensive with the raised portion 3 such that the upper edges of the reagent matrix 2 adjacent to the raised portion 3 are protected axially by the raised portion of the substrate.

A similar embodiment of the invention is illustrated in FIG. 2 which actually illustrates use of double backed adhesive 4 to retain the reagent pad or matrix 2 in place.

Obviously, the substrate 1 in FIGS. 1 and 2 can be formed by any suitable means. The desired shaping of the substrate can be effected mechanically, by pressure rolls, by warming, by extrusion, etc. A combination of techniques is also possible.

FIG. 3 illustrates a substrate with two reagent strips held in place by "press-fit" in depressions in the carrier or substrate 1. Thus, the reagent area 2 of the individual reagent test devices which are cut from the substrate lie protected from damage when an individual reagent test device or reagent strip is wiped. Fraying of the edges and damage to the top of the reagent page are therefore minimized during packaging, handling and transportion.

From the foregoing, it will be seen that this invention is well adapted to attain all of the ends and objects hereinabove set forth, together with other advantages which are obvious and which are inherent to the system. The present invention achieves an objective which has been sought by manufacturers of diagnostic test devices for overcoming the problem of protecting the all important reactive surface of reagent matrix areas from the time the reagent test device is manufactured until the time of actual use. With such areas measuring as small as $\frac{1}{2}$ centimeter by $\frac{1}{2}$ centimeter damage to any area of the reagent pad can distort a measurement which is made rendering the results inaccurate.

Obviously, many other modifications and variations of the invention as hereinbefore set forth can be made without departing from the spirit and scope of the invention.

What is claimed is:
1. A test device comprising:
   (a) an elongated substrate having a first horizontal portion and a raised portion, said raised portion sloping upwardly from said first horizontal portion to a first termination point and then perpendicularly downward toward a second horizontal portion to form a right angle shoulder, said second horizontal portion further comprising a second termination point whereby said raised portion then slopes downwardly back to said first horizontal portion, whereby a wiping force moving axially across said first horizontal portion will first move gradually up to said second horizontal portion and then move gradually down substantially to the plane of said first horizontal portion, and
   (b) a reagent matrix positioned on a said second horizontal portion and abutting said raised portion at said right angle shoulder wherein the height of said reagent matrix is coextensive with said raised portion at said first and second termination points whereby the upper edge of said reagent matrix adjacent said raised portion is protected by the raised portion.

2. A test device according to claim 1 wherein the substrate is a plastic material.

3. A test device according to claim 1 in which the substrate is selected from the group consisting of polyethylene, polypropylene, polyamide, polyester and polystyrene films.

* * * * *